(12) United States Patent
Haiat et al.

(10) Patent No.: US 11,864,775 B2
(45) Date of Patent: Jan. 9, 2024

(54) DEVICE FOR ASSESSING THE SOLIDITY OF A MATERIAL

(71) Applicants: Centre National de la Recherche Scientifique, Paris (FR); Université Paris XII Val de Marne, Creteil (FR)

(72) Inventors: Guillaume Haiat, Rungis (FR); Alexis Hubert, Alfortville (FR)

(73) Assignees: Centre National de la Recherche Scientifique, Paris (FR); Université Paris XII Val de Marne, Creteil (FR)

( * ) Notice: Subject to any disclaimer, the term of this patent is extended or adjusted under 35 U.S.C. 154(b) by 485 days.

(21) Appl. No.: 17/263,392

(22) PCT Filed: Jul. 25, 2019

(86) PCT No.: PCT/EP2019/070131
§ 371 (c)(1),
(2) Date: Jan. 26, 2021

(87) PCT Pub. No.: WO2020/021046
PCT Pub. Date: Jan. 30, 2020

(65) Prior Publication Data
US 2021/0161576 A1    Jun. 3, 2021

(30) Foreign Application Priority Data
Jul. 26, 2018    (FR) ..................... 1856960

(51) Int. Cl.
*A61B 17/16*        (2006.01)
*A61B 17/92*        (2006.01)
(Continued)

(52) U.S. Cl.
CPC ........ *A61B 17/1604* (2013.01); *A61B 5/4504* (2013.01); *A61B 5/4509* (2013.01);
(Continued)

(58) Field of Classification Search
CPC ... A61B 5/4504; A61B 5/4509; A61B 5/4514; A61B 17/1604; A61B 17/92;
(Continued)

(56) References Cited

U.S. PATENT DOCUMENTS 2,955,456 A     10/1960 Jensen et al.
2015/0282856 A1*  10/2015 Haiat .................... A61F 2/4609
                                                        606/100

FOREIGN PATENT DOCUMENTS

EP          2923677 A1    9/2015
WO      2017206741 A1    12/2017

OTHER PUBLICATIONS

International Search Report issued in International Application No. PCT/EP2019/070131, dated Dec. 6, 2019 (5 pages).
(Continued)

*Primary Examiner* — Larry E Waggle, Jr.
(74) *Attorney, Agent, or Firm* — Osha Bergman Watanabe & Burton LLP

(57) ABSTRACT

A device for assessing the solidity of a material comprising an ancillary tool (2) having an end (2B) in the form of a point or blade, an impactor (4) for striking the ancillary tool (2), a sensor (12) and a processing unit (30). The ancillary tool (2) is placed between a material (8) and the impactor (4) and transmits the impact force generated by the impactor (4) to the material (8). The sensor (12) is capable of measuring a quantity from among the impact force and the deformation of the impactor, and of supplying a measurement signal. The processing unit (30) is suitable for calculating, from the measurement signal, an indicator representative of the solidity of the material (8). The indicator corresponds to the duration of a time window between the first peak (P1) of maximum amplitude of the measurement signal and the second peak of maximum amplitude (P2).

12 Claims, 3 Drawing Sheets

(51) Int. Cl.
  *G01N 3/34*   (2006.01)
  *A61B 90/00*  (2016.01)
  *A61B 5/00*   (2006.01)
  *G01N 3/30*   (2006.01)

(52) U.S. Cl.
  CPC ............ *A61B 5/4514* (2013.01); *A61B 17/92* (2013.01); *G01N 3/30* (2013.01); *G01N 3/34* (2013.01); *A61B 2090/064* (2016.02); *A61B 2562/0252* (2013.01); *G01N 2203/0039* (2013.01); *G01N 2203/0076* (2013.01)

(58) Field of Classification Search
  CPC ........ A61B 2090/064; A61B 2090/065; A61B 2562/0252; G01N 3/30; G01N 3/34; G01N 2203/001; G01N 2203/0032; G01N 2203/0039; G01N 2203/0076
  See application file for complete search history.

(56) References Cited

OTHER PUBLICATIONS

Written Opinion issued in International Application No. PCT/EP2019/070131; dated Dec. 6, 2019 (12 pages).
Office Action issued in Indian Application No. 202147007487; dated Oct. 31, 2022 (6 pages).
Office Action issued in counterpart Chinese Patent Application No. 201980063643.1 dated Sep. 27, 2023 (19 pages).
F. Yueguang; "Orthopaedic and Traumatology Surgery"; Shanghai Science and Technology Publishing House, p. 7; Feb. 29, 2012 (3 pages).

* cited by examiner

DEVICE FOR ASSESSING THE SOLIDITY OF A MATERIAL

TECHNICAL FIELD

The invention relates to a device for assessing the solidity of a material. Such a device can be used, notably, to assess the solidity of a tissue such as, for example, bone or cartilage during a surgical operation, in particular during an osteotomy.

BACKGROUND

An osteotomy is a surgical operation consisting in cutting, fracturing or shaping a bone or cartilage, in order to remedy a deformity. It is generally carried out using a surgical chisel of suitable form, called osteotome, and a mallet. The practitioner holds the osteotome in contact with the bone or the cartilage and strikes the osteotome end which is not in contact with the tissue using a mallet, in order to cut, fracture or shape the bone or the cartilage.

There is currently no device that makes it possible to satisfactorily and in real time control the position and the progress of the osteotome in the organ of the patient (e.g. in the nose of the patient). The use of a buttoned osteotome allows the practitioner to follow the progress of the osteotome under the skin, but proves inadequate for controlling the position of the osteotome with respect to the tissues. The practitioner relies also on the noise generated and on his or her experience to adapt the intensity and the number of impacts as well as the strike angle. However, this approach is purely empirical, depends on the practitioner and lacks reliability. Approaches of X-ray type (image intensifier) cannot be used easily because they are too difficult to put in place and ionizing for the patient and for the practitioner. The approaches of MRI type cannot be used because of the cost and availability of the equipment.

To be able, during an osteotomy, to assess the solidity of the tissue in contact with the cutting end of the osteotome would allow the practitioner to have an idea:

of the nature of this tissue, e.g. cartilage or bone,
of the solidity of the bone impacted, and/or
of the occurrence of cracks in the impacted bone.

The practitioner could then better assess the positioning and the progress of the osteotome in the tissues, the intensity and the number of impacts necessary to fracture the bone and the moment from which the bone is fractured.

In this context and, more generally, in the context of collecting information on any material, one aim of the invention is to propose a device that makes it possible to assess the solidity of a material being struck by means of an ancillary tool.

GENERAL DESCRIPTION

The invention relates to a device for assessing the solidity of a material comprising: an ancillary tool having opposite first and second ends, the second end having the form of a point or blade, an impactor adapted for striking on the first end of the ancillary tool, at least one sensor and a processing unit.

The ancillary tool is adapted for being placed between a material and the impactor, with its second end in contact with the material, and for transmitting the impact force generated by the impactor to the material.

The sensor is capable of measuring a quantity from among the impact force generated and the deformation of the impactor, and of supplying a measurement signal representing the variation in time of said quantity upon an impact.

The processing unit is adapted for calculating, from the measurement signal, an indicator representative of the solidity of the material.

The proposed solution therefore relies on the implementation of one or more sensors associated with the impactor and delivering a measurement signal, the recording and analysis of this signal making it possible to determine an indicator indicative of the solidity of the material. When several sensors are used, the signals respectively delivered by these sensors can be, for example, averaged or combined to obtain the measurement signal which will be analyzed and on the basis of which the indicator will be calculated.

Such a device makes it possible, for example during an osteotomy, to inform the practitioner on the solidity of the material, bone or cartilage, in contact with the osteotome.

In another example, the ancillary tool is a needle intended to be inserted into a biological tissue. The analysis of the signals obtained upon the impact on the needle allows the practitioner to assess the solidity of the tissue in proximity to the second end, i.e. the point, of the needle.

In addition to its low cost, this device has the advantage of being simple to use. In particular, with this device, the gestures of the practitioner during the operation remain the same. The practitioner does not therefore have to learn new gestures and can exploit the experience that he or she has already acquired with conventional tools (ancillary tool and impactor).

The proposed indicator corresponds to the duration of a time window. The start of this time window is defined with respect to an instant corresponding to the first peak of maximum amplitude of the measurement signal and the end of this time window is defined with respect to an instant corresponding to the second peak of maximum amplitude of the measurement signal. It has been demonstrated that the indicator thus calculated was correlated with the solidity of the material in contact with the ancillary tool, which itself depends on the geometry of the material, on the mechanical properties thereof, on the presence of cracks in the material, etc.

In some embodiments, the processing unit detects, in the measurement signal, the first peak of maximum amplitude and the maximum amplitude peak succeeding the first peak, this latter peak being considered as the second peak of maximum amplitude only if the measurement signal becomes lower than a predetermined limit value between these two peaks (i.e. if the measurement signal drops below the limit value before going back above this value to form the second peak). In particular, the limit value can lie between 1 and 20% of the maximum amplitude of the first peak. For example, the maximum amplitude peak succeeding the first peak is considered as the second maximum amplitude peak only if the measurement signal passes below a limit value equal to 5% of the maximum amplitude of the first peak.

This precaution makes it possible to avoid measurement errors linked to a phenomenon of duplication of the first peak, which has been observed in a small number of cases. Upon such a phenomenon, the two peaks obtained by duplication of the first peak are close to one another and the inventors realized that the measurement signal did not have time to decrease significantly between these two peaks. So, the solution consisting in checking that the measurement signal has decreased sufficiently before reaching the second maximum amplitude peak makes it possible to avoid wrongly considering the duplicate of the first peak as the second peak of maximum amplitude, and therefore avoid an indicator measurement error. Of course, other methods of analyzing the measurement signal could be envisaged for detecting a duplication of the first peak and avoiding measurement errors in such a case.

In some embodiments, the device comprises, in addition, an alert system linked to the processing unit and cooperating therewith so as to emit an alert signal when the indicator crosses a predetermined threshold value. This threshold value can be determined by trial and error. Of course, other conditions relating to the indicator itself, or to the variation of the indicator upon a series of successive impacts, could be used to trigger an alert, without departing from the scope of the invention. In the context of a surgical operation, the alert can allow the practitioner to stop striking the ancillary tool with the impactor.

In some embodiments, the ancillary tool is a chisel, a punch or a needle. In particular, it can be a surgical chisel or osteotome.

In some embodiments, the impactor has a strike face adapted for striking the ancillary tool and the sensor is a force sensor capable of measuring the impact force and of supplying a measurement signal representing the variation in time of the impact force upon an impact. In this case, the force sensor is, preferably, fixed to the strike face.

In other embodiments, the impactor has a strike face adapted for impacting the impact surface, a face opposite the strike face and lateral faces extending between the strike face and the opposite face, and the sensor is a deformation sensor capable of measuring the deformation of the impactor and of supplying a measurement signal representing the variation in time of the deformation of the impactor upon an impact. In this case, the deformation sensor is, preferably, fixed to one of the lateral faces of the impactor.

In some embodiments, the impactor is a hammer, or equivalent, and comprises a handle topped by a strike head. In particular, the impactor can have substantially the same shape and the same weight as the impactors routinely used hitherto. Thus, experienced practitioners are immediately able to handle the impactor correctly.

It will be noted that the impactor exerts the impact force on the material via the ancillary tool. In other words, the impact force is generated on the ancillary tool and transmitted thereby to the material.

The invention relates also to a method for assessing the solidity of a material, in which:
  a device as previously described is provided,
  the ancillary tool is struck using the impactor, the ancillary tool being placed between the impactor and a material, with its second end in contact with the material, so as to transmit the impact force generated by the impactor to the material,
  the indicator is calculated from the measurement signal supplied by the sensor, and
  the solidity of the material is assessed on the basis of the indicator.

The ancillary tool can be, but is not necessarily, an osteotome. In this case, the impactor is used to strike the osteotome previously inserted into the body of a patient (e.g. into the nose), so as to obtain the measurement signal, and, on the basis of the indicator, the solidity of the material in contact with the second end, i.e. the blade, of the osteotome, is determined. It is then possible to deduce information therefrom on the position of the osteotome in the body, on the thickness of the material, on the state (cracked or not) of the material, etc.

The ancillary tool can also be a needle. In this case, the impactor is used to strike the needle previously inserted into a biological tissue, so as to obtain the measurement signal, and, on the basis of the indicator, the solidity of the tissue in contact with the second end, i.e. the point, of the needle, is determined. The analysis of the signals obtained upon the impact on the needle allows the practitioner to assess the solidity of the tissue.

The advantages of such a method follow from the advantages of the device used.

The features and advantages mentioned above, and others, will become apparent on reading the following detailed description of exemplary embodiments of the proposed device. This detailed description refers to the attached drawings.

BRIEF DESCRIPTION OF THE DRAWINGS

The attached drawings are schematic and are not to scale, their purpose is primarily to illustrate the principles of the invention.

DETAILED DESCRIPTION

Figure 1:
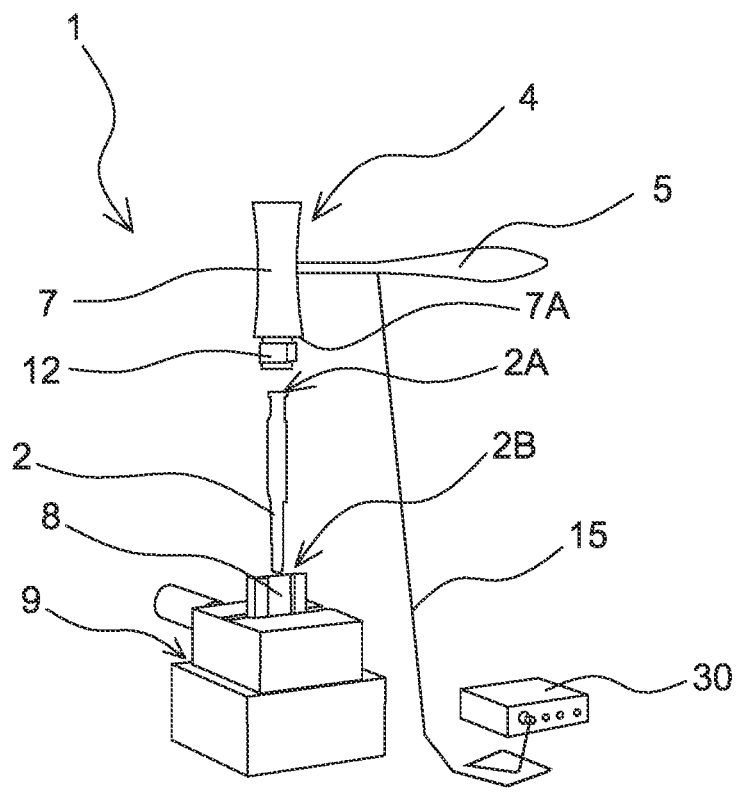
FIG. 1 is a schematic representation of a setup comprising an ancillary tool, an impactor, a sensor, a processing unit and a sample of material struck using the ancillary tool.

Figure (FIG. 1 represents an example of a device 1 for assessing the solidity of a material. This device 1 comprises an ancillary tool 2 having a first end 2A and a second end 2B opposite the first end 2A. The second end 2B has the form of a blade: it is thin, tapered and ends with an edge. The ancillary tool 2 is, for example, a surgical chisel, or osteotome, of the type used for rhinoplasty operations. The experimental results described below were obtained with an osteotome 10 mm wide (length of the blade) marketed by the company Zepf, Tuttlingen, Germany, under the reference 32-6002-10.

The device 1 also comprises an impactor 4 of hammer or equivalent type, comprising a handle 5 topped by a strike head 7. The ancillary tool 2 and the impactor 4 are adapted for striking, or impacting, the first end 2A with the impactor 4. The impactor 4 is, for example, a surgical mallet 5. The experimental results described below were obtained with a 260 grams surgical mallet marketed by the company Zepf, Tuttlingen, Germany, under the reference 32-6906-26.

The impactor 4 is equipped with a force sensor 12 capable of measuring the impact force generated by the impactor 4 to supply a measurement signal representing the variation in time of the impact force upon an impact. The sensor 12 is capable of converting the impact force applied to the assembly formed by the ancillary tool 2 and the material 8 upon each strike into a usable electrical signal. It is, for example, a load cell or a piezoelectric sensor connected, according to an appropriate setup, to a processing unit 30. In the example represented, the force sensor 12 is fixed to the strike face 7A of the head 7 of the impactor 4. For example, it is screwed to the center of the strike face 7A. As a variant, the force sensor 12 can be positioned at the first end 2A of the ancillary tool. The experimental results described below were obtained with a piezoelectric force sensor marketed by the company PCB Piezotronics, Depew, NY, United States, under the reference 208C04, with a current measurement range up to 4.45 kN in compression.

The device also comprises a processing unit 30 coupled to the sensor 12 and configured to process the measurement signals delivered by the sensor 12. This processing unit 30 comprises, for example, a microcontroller. The processing unit 30 can be housed in an external housing. As a variant, the processing unit 30 can be incorporated in the impactor 4. According to another variant, the processing unit 30 can be formed by separate elements such as a microcomputer linked to a data acquisition module which is in turn linked to the sensor 12. The link between the sensor 12 and the processing unit 30 is, in the example of FIG. 1, wired by means of a cable 15. As a variant, the measurement signals supplied by the sensor 12 can be transmitted by means of a wireless link, in which case the sensor 12 is equipped with an antenna or equivalent, allowing the transmission of the measurement signals to the processing unit 30.

The experimental results presented hereinbelow were obtained with a processing unit 30 comprising a "LabVIEW" acquisition module marketed under the reference NI 9234 by the company National Instruments, Austin, TX, United States, with a sampling frequency higher than 50 kHz. In the example, the sampling frequency was 51.2 kHz and the resolution was 24 bits. This module was used to record the change in the force exerted by the impactor 4 over time. The data were transferred to a computer via a "LabVIEW" graphical interface for a measurement time of 10 ms or less.

The ancillary tool 2 and the impactor 4 are used to strike a sample of material 8. For this, the second end 2B of the ancillary tool 2 is placed in contact with the sample of material 8 and the ancillary tool 2 is impacted by the impactor 4 so that the impact force generated by the impactor 4 is transmitted to the material 8 by the ancillary tool 2. For the tests, the sample is immobilized, for example by being clamped in a vice 9. Upon each impact, the sensor 12 measures the impact force generated and supplies a measurement signal representing the variation in time of this force during the impact. The impact is considered to begin from the instant when the impactor 4, the ancillary tool 2 and the material 8 are in contact with one another and lasts for a certain time period after this instant. This time period is less than 50 ms. An example of the signal supplied by the sensor 12 is represented in FIG. 2 and described below.

The inventors had the idea of focusing on such a measurement signal and have demonstrated that this signal conveyed information on the solidity of the material 8. In particular, the inventors have succeeded in determining, from the measurement signal collected, an indicator representative of this solidity, as explained hereinbelow.

To try to explain the link between the measurement signal collected and the solidity of the material 8, the following explanation can be put forward. The impactor 4 generates, on the sample of material 8, via the ancillary tool 2, an impact force which is the source of vibration modes throughout the system formed by the impactor 4, the sensor 12, the ancillary tool 2 and the material 8 when these elements are all in contact at the time of impact. These vibration modes depend on the solidity of the material 8. Schematically, the more solid the material 8, the more rigid the system and the higher the resonance frequencies of the vibration modes.

Figure 2:
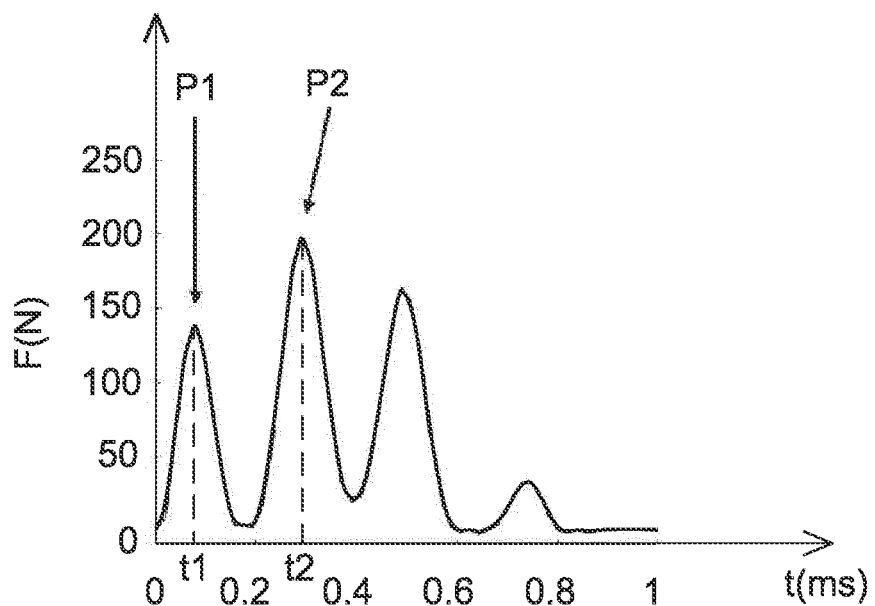
FIG. 2 schematically represents an example of a signal obtained using the sensor of FIG. 1, when a blow is delivered on the sample.

FIG. 2 is a graph schematically representing an example of a signal obtained using the force sensor 12 upon an impact on a sample. The time (t) in milliseconds (ms) is given on the x axis, the force (F) in Newtons (N), measured by the sensor 12, is given on the y axis.

The signal of FIG. 2 corresponds to an impact or blow. The impact is made at the time t=0. The first maximum amplitude peak P1 appears rapidly (i.e. less than 0.1 millisecond after) at the time t1. The second maximum amplitude peak appears just after the first peak P1 (i.e. a little more than 0.1 millisecond after) at the time t2. The inventors have demonstrated that this period (t2-t1) between the first and second peaks P1, P2 was a reliable and relevant indicator IN for reflecting the solidity of the material.

The tests described below, with reference to the attached figures, illustrate the link between the indicator IN and the solidity of the material. The materials tested were ordinary birch plywood (3 ply), polycarbonate (Nudec, Barcelona, Spain), a polyurethane resin (SmoothCast 300, Smooth-On, Eaton, PA, United States) and "ORTHObone" artificial bone (3B Scientific, Hamburg, Germany) of three different densities (ORTHObone 10 PCF, 20 PCF and 30 PCF). These materials are respectively denoted "PW", "PC", "RS", "O1", "O2" and "O3". Each material was subdivided into samples of 3×4.5 cm with thicknesses varying between 2 and 8 mm, for a total of 100 samples. Each sample thus had the form of a wafer. Each wafer was placed vertically and clamped in the vice 9, the cutting edge of the end 2B of the ancillary tool 2 being at right angles to the wafer, as represented in FIG. 1. In other words, the thickness-wise direction of the sample was parallel to the edge of the blade of the ancillary tool 2. Thus, the thickness of the sample corresponds, in this example, to the length of the zone of contact between the sample and the cutting edge of the blade-form end 2B of the ancillary tool 2. Moreover, the length (i.e. the overall length) of the cutting edge is greater than the length of the zone of contact between the sample and the cutting edge.

The thickness of each sample was measured using a Vernier caliper. The mechanical properties, the mean and the standard deviation of the distribution of the thicknesses for the six materials tested are given in the table hereinbelow in which "E" designates the Young's modulus in MPa, "tan delta" denotes the damping factor or loss factor corresponding to the viscoelasticity of the material, "$d_m$" and "sigma d", in mm, respectively denote the mean and the standard deviation of the distribution of the thicknesses for each material, "$d_-$" denotes the minimum thickness in mm, "$d_+$" denotes the maximum thickness in mm and N the number of samples for each material.

| Material | E (MPa) | tanδ | $d_m$ (mm) | $σ_J$ (mm) | $d^-$ (mm) | $d^+$ (mm) | N |
|---|---|---|---|---|---|---|---|
| PW | 2400 | 0.01 | 4.7 | 1.5 | 3.0 | 6.0 | 11 |
| PC | 1300 | 0.02 | 4.9 | 1.2 | 3.0 | 6.0 | 20 |
| RS | 500 | 0.03 | 4.7 | 1.5 | 2.4 | 6.8 | 17 |
| O1 | 41 | 0.03 | 4.4 | 1.4 | 2.4 | 7.1 | 18 |
| O1 | 250 | 0.03 | 4.1 | 1.5 | 2.5 | 7.1 | 15 |
| O3 | 380 | 0.03 | 4.5 | 1.2 | 2.1 | 5.8 | 19 |

Figure 3:
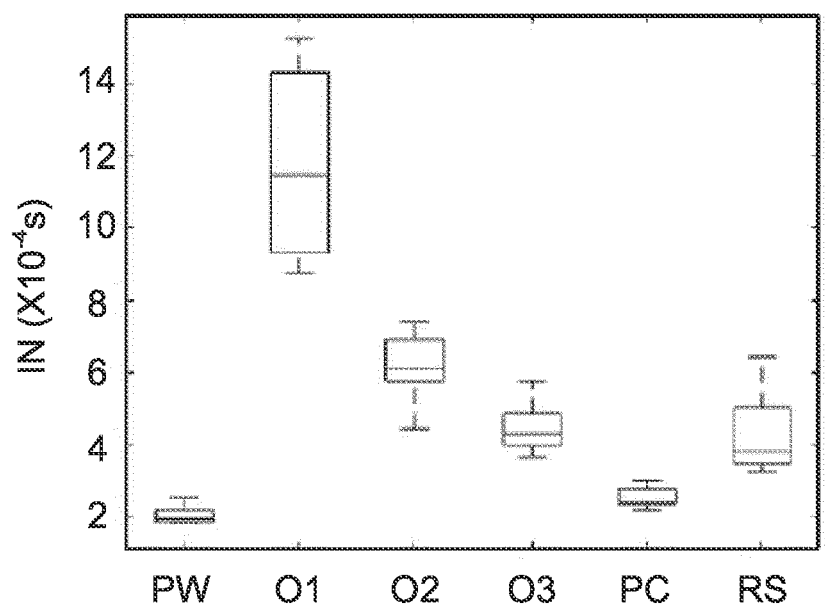
FIG. 3 represents the values of the indicator for different types of materials.

FIG. 3 is a graph representing, in box plot form, the distribution of the indicator IN for the different types of material 8. The indicator IN is expressed in tenths of a millisecond ($10^{-4}$ s) and given on the y axis. The type of material 8 is given on the x axis. The central horizontal bar indicates the median and the top and bottom sides of the box indicate the upper and lower quartiles. The whiskers extend to the extreme values of the distribution. The values of FIG. 3 are grouped together according to the types of material only, with no consideration as to the thickness of the samples. However, as discussed later, the thickness has an impact on the indicator IN and inevitably induces a portion of the dispersion of values observed.

FIG. 3 shows that the type of material has a significant influence on the indicator IN. Generally, the higher the Young's modulus of the material, and therefore the more rigid the material, the more the indicator IN decreases. The Tukey-Kramer tests indicate that the results obtained are significantly different from one type of material to another, except for two pairs of different materials: the pair PW and PC, and the pair O3 and RS.

Figure 4:
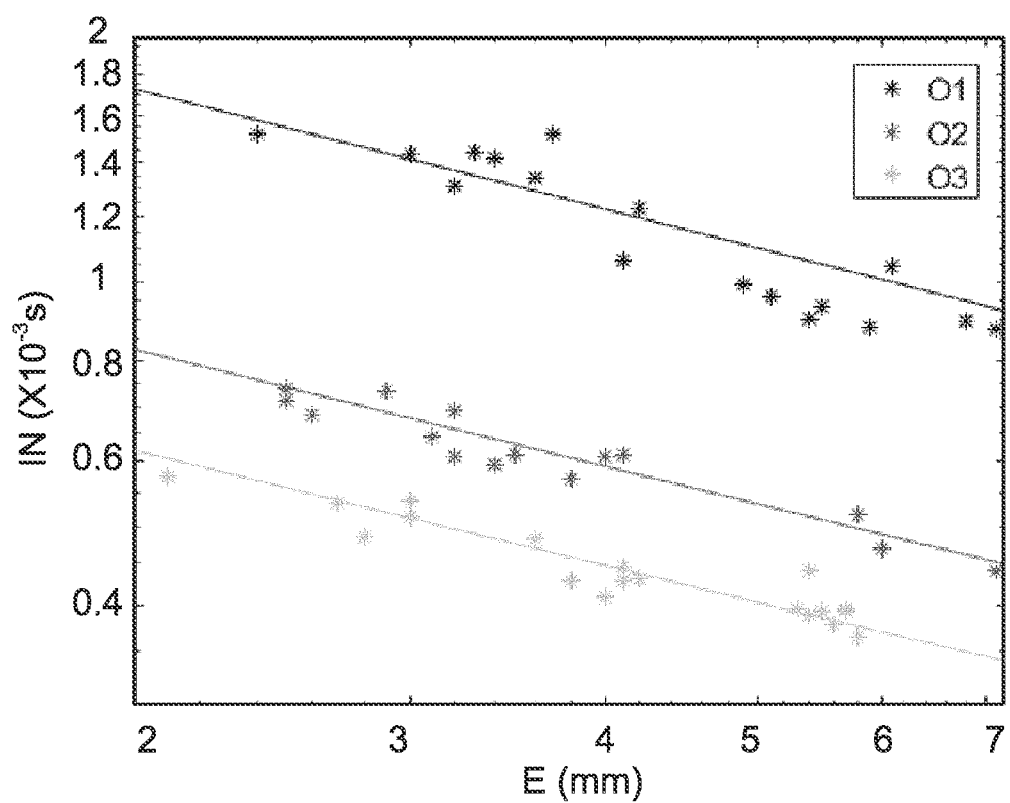
FIG. 4 represents the variation of the indicator for three different materials, when the thickness of the sample varies.

FIG. 4 represents the variation of the indicator IN for three different materials, namely the artificial bones O1, O2 and O3, when the thickness of the sample varies. FIG. 4 shows that the thickness of the sample has a significant influence on the indicator IN. Generally, the greater the thickness, the more the indicator IN decreases.

FIGS. 3 and 4 therefore show that the indicator IN varies as a function of the length of the zone of contact between the sample and the cutting edge of the tool, and as a function of the Young's modulus of the constituent material of the sample. In other words, the indicator IN varies as a function of the thickness of the sample and of the rigidity of the constituent material of the sample.

It should be noted that the solidity of the sample increases as a function of its rigidity (in the case of a biological tissue) and of its thickness. Furthermore, FIGS. 5 and 6, described later, show that the indicator IN varies when a crack appears in the sample. Ultimately, it is understood that the indicator IN is linked, generally, to the solidity of the material of the sample: the more solid this material is because of its rigidity, its significant thickness or the absence of cracks, the lower the indicator IN becomes. Conversely, the more brittle the material, because of its lack of rigidity, its small thickness or the presence of cracks, the higher the indicator IN. It is understood that, in the present explanation, the concept of "solidity" of the material should be understood to be a combination of the thickness of the material, of its physical rigidity and of the presence or not of cracks.

Figure 5:
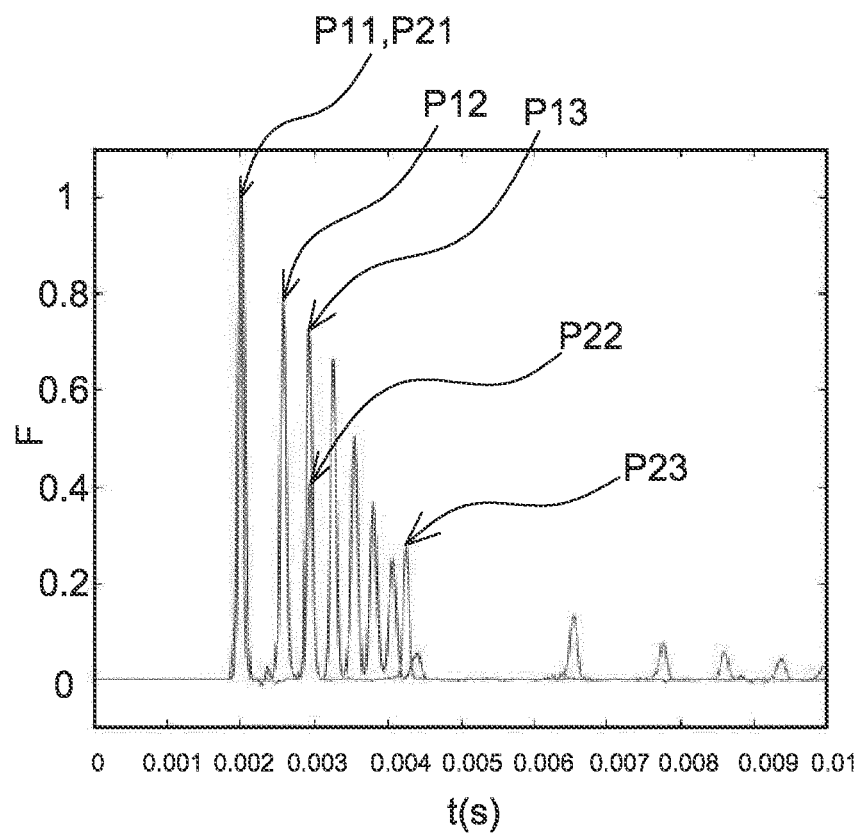
FIG. 5 represents two examples of signals obtained for one and the same sample, one before fracturing of the sample, the other after fracturing.

FIG. 5 is a graph with, on the y axis, the force "F" measured by the sensor expressed in standardized units and, on the x axis, the time "t" in seconds. FIG. 5 represents two examples of signals obtained for one and the same sample, one before fracturing of the sample, the other after fracturing. The first three peaks of the signal before fracturing are denoted P11, P12, P13 and the first three peaks of the signal after fracturing are denoted P21, P22, P23. It can be seen that the indicator IN, which corresponds to the period between the first two peaks P11, P12 or P21, P22, increases significantly once the sample is fractured, i.e. once a crack has appeared in the sample.

Figure 6:
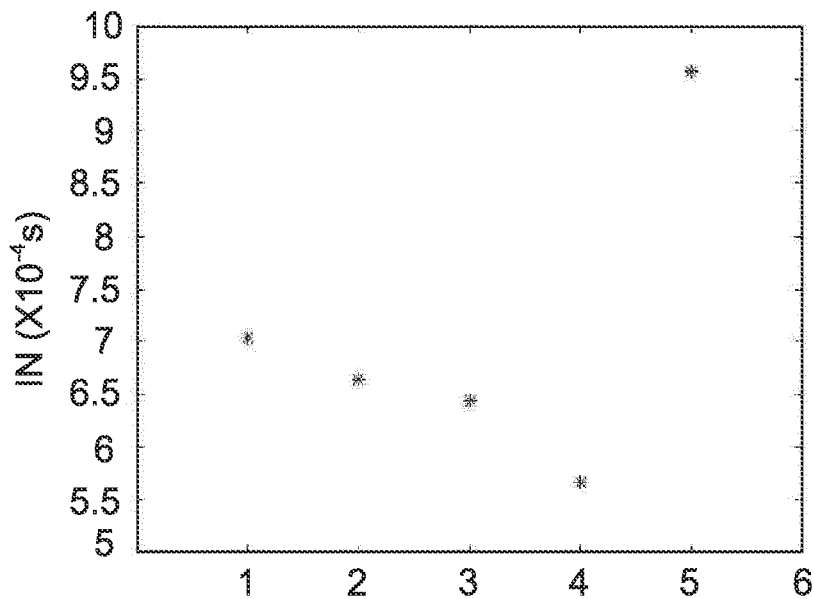
FIG. 6 represents the variation of the indicator upon successive blows delivered to one and the same sample, one of the blows causing a fracture in the sample.

FIG. 6 is a graph representing the change in the indicator IN as a function of the number of impacts made on the sample. The number of impacts (from 1 to 5) is given on the x axis. The indicator IN, expressed in tenths of a millisecond (ms), is given on the y axis. In this example, the appearance of a crack was noted in the sample between impacts number 4 and 5. It can be seen that the indicator IN increases significantly because of the appearance of this crack.

Based on tests equivalent to that of FIG. 6, it is possible, for one and the same material having substantially the same thickness, to determine a threshold value S1 for the indicator IN beyond which the appearance of a crack in the material has necessarily taken place. In the example of FIG. 6, the threshold value S1 could be chosen equal to $8.5 \times 10^{-4}$ s. Obviously, that is only an example.

Once determined, the threshold value S1 can be used to parameterize the device 1. This threshold value S1 is, for example, saved in the memory of the processing unit 30. Furthermore, the device 1 can comprise an alert system (not represented) for emitting an alert signal (for example, a sound, visual and/or touch signal). The alert signal is linked to the processing unit 30 and cooperates therewith to alert the practitioner when the appearance of a crack is detected on the basis of the indicator IN, for example when the indicator IN goes above the threshold value S1. Another embodiment can consist in detecting an abrupt variation of the indicator IN between two successive impacts, which is likely to be linked to the appearance of a crack.

As an example, the device 1 which has just been described can be used in an osteotomy. This surgical operation consists in using an osteotome as ancillary tool 2, and in introducing this osteotome into the nose of a patient in order to induce a green-stick fracture in the bone and the cartilage. This allows the shape of the nose to be subsequently modified. This fracture is produced by impacting the osteotome using the impactor 4. This intervention is considered to be fairly difficult because it is carried out mostly by introducing the osteotome under the skin, which makes it difficult to know the real position of the cutting edge. By using the proposed device, the surgeon will be able, notably, to assess the position of this cutting edge.

Indeed, assessing the solidity of the tissues in contact with the cutting edge of the osteotome, via the indicator IN, allows the practitioner to know whether this cutting edge is situated in the cartilage or in the bone of the nose, these tissues not having the same solidity. The practitioner can then adapt the energy delivered upon the impacts. If the cutting edge is situated in the bone, the practitioner must strike more strongly, whereas, in the cartilage, he or she should be more measured in the impacts in order not to induce additional wounds.

The tracking of the indicator IN, in particular the overshooting of the threshold value S1 or an abrupt increase in IN between two successive impacts, also makes it possible to alert the practitioner to the appearance of a crack in the bone. The practitioner can then stop impacting, the presence of uncontrolled cracks potentially leading to post-operation complications. It is therefore understood that the tracking of the indicator IN makes it possible to assess the solidity of the bone and, more generally, of the material tested, while preventing the appearance of uncontrolled cracks in this material. In this sense, the assessment made is non-destructive.

Finally, the tracking of the indicator IN makes it possible to assess the thickness of the bone in contact with the cutting edge, because this thickness increases progressively as far as the frontal bone, at the precise point where the fracture lines meet and where the surgeon must stop impacting to avoid perforating the frontal bone. This sudden increase in the thickness of the bone indicates the start of the frontal bone and is reflected by a sudden decrease in the indicator IN. It is important at this stage for the practitioner to stop impacting the osteotome because there is a risk of complete fracturing of the nose, which can lead to damage to the blood vessels and serious complications.

The example of use which has just been described is given in an illustrative and nonlimiting manner, a person skilled in the art being easily able to exploit the device and the indicator proposed by the inventors in applications other than an osteotomy, including in non-surgical applications.

Furthermore, the example which has just been described implements a force sensor 12. According to another example (not represented), it is possible to use a deformation sensor capable of supplying a measurement signal representing the variation in time of the deformation of the impactor 4 upon an impact. Such a deformation sensor is capable of converting the deformation of the strike head 7 of the impactor 4 into a usable electrical signal. In this case, instead of being situated on the strike face 7a like the force sensor 12, the deformation sensor is positioned on one of the lateral faces of the strike head 7. In this particular case, the deformation sensor can be positioned on the lateral face extending parallel to the direction of the axis of the handle 5. More specifically, seen from the side, the deformation sensor can be fixed on the front part of the lateral face, between the strike face 7A and the axis of the handle 13. The front and rear are defined here with respect to the striking motion of the impactor 4. The deformation sensor is fixed to the strike head 7, for example by bonding or any other appropriate fixing means, such that the deformation of the strike head 7 causes the deformation of the sensor. The sensor is, for example, a load cell comprising an elastic measurement element whose deformation is first of all converted into a variation of electrical resistance of the gauge, to then generate an electrical output signal. As a variant, it can be a piezoelectric sensor relying on the piezoelectric properties of a material (e.g. of quartz or synthetic ceramics) which generates an electrical charge when it is deformed.

The measurement signal supplied by such a deformation sensor and representing the variation in time of the deformation of the impactor upon an impact also exhibits first and second maximum amplitude peaks. The time period separating these two peaks also proves to be a reliable and relevant indicator for assessing the level of contact between the implant and the receiving bone.

Moreover, the example which has just been described implements an ancillary tool that has an end in the form of a blade. According to another example (not represented), it is possible to use an ancillary tool that has an end in the form of a point, like a punch or a needle.

Finally, the various features of the embodiments or examples described in the present description can be considered in isolation or be combined with one another. When combined, these features can be so combined as described above, or differently, the invention not being limited to the specific combinations previously described. In particular, unless stipulated otherwise or technically incompatible, a feature described in relation to one embodiment or example can be applied likewise to another embodiment or example.

The invention claimed is:

1. A device for assessing a solidity of a material comprising:
   ancillary tool having opposite first and second ends, the second end being in the form of a point or blade,
   an impactor suitable for striking the first end of the ancillary tool,
   at least one sensor, and
   a processing unit,
   wherein the ancillary tool is adapted for being placed between a material and the impactor, with its second end in contact with the material, and for transmitting an impact force generated by the impactor to the material,
   wherein the sensor is capable of measuring a quantity from among the impact force generated and a deformation of the impactor, and of supplying a measurement signal representing a variation in time of said quantity upon an impact,
   wherein the processing unit is adapted for calculating, from the measurement signal, an indicator representative of the solidity of the material, and
   wherein the indicator corresponds to the duration of a time window, a start of this time window being defined with respect to an instant corresponding to a first peak of maximum amplitude of the measurement signal and an end of this time window being defined with respect to an instant corresponding to a second peak of maximum amplitude of the measurement signal.

2. The device as claimed in claim 1, wherein the processing unit detects, in the measurement signal, the first peak of maximum amplitude and a peak of maximum amplitude succeeding the first peak, this latter peak being considered as the second peak of maximum amplitude only if an amplitude of the signal becomes lower than a predetermined limit value between the two peaks.

3. The device as claimed in claim 2, wherein the predetermined limit value lies between 1 and 20% of the first peak of maximum amplitude.

4. The device as claimed in claim 1, comprising, in addition, an alert system linked to the processing unit and cooperating therewith so as to emit an alert signal when the indicator crosses a predetermined threshold value.

5. The device as claimed in claim 1, wherein the ancillary tool is a chisel, a punch or a needle.

6. The device as claimed in claim 1, wherein the ancillary tool is an osteotome.

7. The device as claimed in claim 1, wherein the sensor is fixed to the impactor or to the ancillary tool.

8. The device as claimed in claim 1, wherein the impactor has a strike face adapted for striking the ancillary tool and wherein the sensor is a force sensor fixed to the strike face.

9. The device as claimed in claim 1, wherein the impactor has a strike face adapted for striking the ancillary tool, a face opposite the strike face and lateral faces extending between the strike face and the opposite face, and wherein the sensor is a deformation sensor fixed to one of the lateral faces of the impactor.

10. The device as claimed in claim 1, wherein the second end of the ancillary tool has the form of a blade, and wherein a length of a cutting edge of this blade is greater than a length of a zone of contact between the material and the cutting edge.

11. The device as claimed in claim 1 comprising, in addition, an alert system linked to the processing unit and cooperating therewith so as to emit an alert signal when the indicator varies abruptly between two successive impacts.

12. A method for assessing the solidity of a material, wherein:
   a device according to claim 1 is provided,
   the ancillary tool is struck using the impactor, the ancillary tool being placed between the impactor and a material, with its second end in contact with the material, so as to transmit the impact force generated by the impactor to the material,
   the indicator is calculated from the measurement signal supplied by the sensor, and
   the solidity of the material is assessed on the basis of the indicator.

* * * * *